United States Patent [19]

Verkaart

[11] Patent Number: 4,878,537

[45] Date of Patent: Nov. 7, 1989

[54] HEAT EXCHANGER FOR PHYSIOLOGICAL FLUIDS

[75] Inventor: Wesley H. Verkaart, Duxbury, Mass.

[73] Assignee: Level 1 Technologies, Marshfield, Mass.

[21] Appl. No.: 53,637

[22] Filed: May 26, 1987

Related U.S. Application Data

[63] Continuation-in-part of Ser. No. 866,910, May 27, 1986, Pat. No. 4,759,749.

[51] Int. Cl.⁴ .............................................. A61F 7/12
[52] U.S. Cl. ..................................... 165/156; 604/113
[58] Field of Search .............. 62/259.3; 165/156, 159, 165/163, 164, 154, 46, 67; 604/113; 128/399

[56] References Cited

U.S. PATENT DOCUMENTS

| | | | |
|---|---|---|---|
| 2,316,376 | 4/1943 | Weiss | 165/154 X |
| 3,893,507 | 7/1975 | MacCracken et al. | 165/46 |
| 4,231,353 | 11/1980 | Kanatani et al. | 126/443 |
| 4,231,425 | 11/1980 | Engstrom | 165/156 |
| 4,475,584 | 10/1984 | Martin et al. | 165/154 X |

*Primary Examiner*—Henry A. Bennet
*Attorney, Agent, or Firm*—Berman, Aisenberg & Platt

[57] ABSTRACT

A heat exchanger preferably for use in heating physiological fluids includes an inner conduit, an outer conduit, and end caps which seal the outer conduit to the inner conduit to form a flow channel. The inner conduit is preferably of aluminum and the outer conduit and end caps are of an elastomeric material. The end caps are designed to tightly engage the inner conduit and to be solvent bonded to the outer conduit. When the inner conduit elongates because of thermal expansion, the outer conduit elastically deforms so that there is no relative movement between the end cap and the inner conduit. This preserves sterility during temperature variation.

13 Claims, 1 Drawing Sheet

HEAT EXCHANGER FOR PHYSIOLOGICAL FLUIDS

This application is a continuation-in-part of U.S. Application 866,910 which was filed on May 27, 1986, U.S. Pat. No. 4,759,749.

TECHNICAL FIELD

This invention relates to the art of heat exchangers. In the preferred embodiment, the heat exchanger is used for warming physiological fluids.

BACKGROUND

It is often necessary to warm physiological fluids prior to introducing them into a patient. For example, blood is refrigerated during storage and is preferably warmed before being introduced into a patient during a transfusion. Because it is frequently necessary to warm the physiological fluid rapidly, for example during an emergency medical procedure where a large quantity of fluid is required, heat exchangers have been designed to warm the fluid as it passes from the container the patient.

A heat exchanger for warming blood during a transfusion, is shown in U.S. Pat. No. 2,910,981 (Wilson, et al.). This heat exchanger includes a central tube surrounded by a jacket to form a space between the jacket and tube for circulation of a warming fluid. The fluid to be warmed and administered to a patient passes through the central tube. The central tube and the jacket are integrally formed, and three-port valves are screwed into threaded receptables at opposite ends of the heat exchanger to provide access to the central tube.

U.S. Pat. No. 3,643,733 (Hall) shows a heat exchanger wherein an outer tube partially covers an inner tube, the inner tube having fins which extend into the space between the inner and outer tubes for increasing heat transfer. Because of the different coefficients of expansion between the materials used in fabricating the inner and outer tubes, differential expansion occurs when the warming fluid begins to flow. To accommodate this differential expansion, Hall teaches an end bell held to an end of the outer tube by a spring and movable with respect to the inner tube.

The Hall heat exchanger is complicated in construction and permits a violation of sterility by movement of the end bell along the inner tube.

SUMMARY OF THE INVENTION

In accordance with the invention, a heat exchanger is provided which is extremely simple to manufacture and which maintains sterility even during temperature changes. In accordance with the invention, an outer tube surrounds an inner tube to provide a space between the two tubes for receiving a fluid to be warmed. End caps at opposite ends of the outer tube provide access to the space. A warming fluid passes through the inner tube, and heat is transmitted from the inner tube to the fluid to be warmed. The coefficients of expansion of the inner and outer tubes are different, and one of the tubes and/or the end caps is made of an elastic material whereby thermal expansion or contraction of the other tube is accommodated by elastic expansion or contraction of the one tube or end caps. By this construction, end caps may be secured to the outer and inner tubes to prevent movement during expansion to preserve sterility.

In a preferred embodiment, the inner tube is fabricated of a metal having a high heat conductivity, preferably aluminum. The outer tube is fabricated of an elastomeric material, such as polyvinylchloride, and the end caps are similarly fabricated of polyvinylchloride.

While the inner tube may be a straight, smooth cylindrical element, it is preferably provided with a twisted tubular center area between the end cap seals which provides a helical exterior surface to cause the fluid to be warmed to follow a helical path.

DETAILED DESCRIPTION OF THE INVENTION

Figure 1:
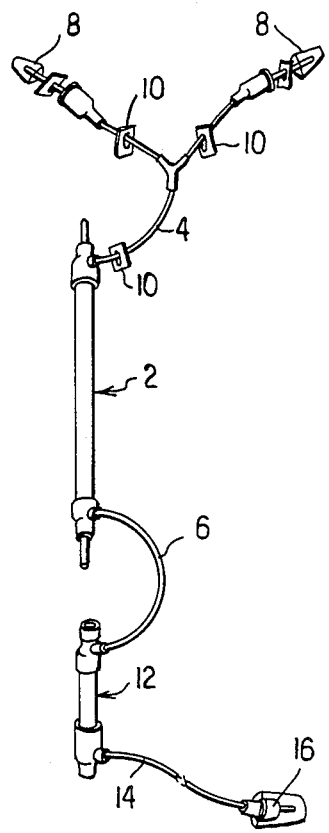
FIG. 1 is a perspective view of a heat exchanger in accordance with the invention in combination with a filter.

With reference to FIG. 1, a heat exchanger 2 in accordance with the invention is shown having a tube 4 attached to an inlet end, and a tube 6 attached at an outlet end. Tube 4 is connected through a Y-connector to bag spikes 8. Each of the tubes may have a flow controller 10 thereon for deforming the tubes to control the liquid flow.

A filter and air eliminator 12 is connected to heat exchanger 2 by tube 6, and a tube 14 extends from the outlet of filter 12 to a connector 16 for passing a physiological fluid to a patient.

Spikes 8 are designed to be connected to bags, which are known in the art, containing a physiological fluid, such as blood, to be administered to a patient.

Figure 2:
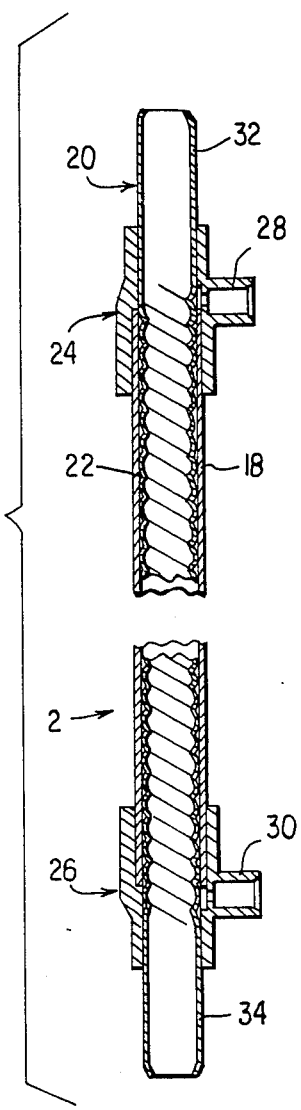
FIG. 2 is a longitudinal cross section of the heat exchanger shown in FIG. 1.

FIG. 2 is a longitudinal cross section of the heat exchanger shown in FIG. 1. The heat exchanger comprises an outer conduit 18 which partially surrounds an inner conduit 20. The outer conduit is spaced from the inner conduit to provide a flow channel 22, which in the preferred embodiment is a helical path. Outer conduit 18 is sealed and secured to inner conduit 20 at opposite ends by end caps 24 and 26, which are preferably identical. End cap 24 includes a tubing connector 28, and end cap 26 includes a similar tubing connector 30.

Inner conduit 20 extends beyond end caps 24 and 26 to provide a first connecting projection 32 and a second connecting projection 34. In use, connecting projections 32 and 34 engage connecting blocks of a fluid supply system whereby a warming fluid is supplied to the inner conduit 20. As shown in FIG. 1, sections of flexible tubing are connected to tubing connectors 28 and 30 for supplying a physiological fluid to flow channel 22.

Inner tube 20 is made of a bio-compatible metal which is preferably aluminum and may be anodized or otherwise coated. Inner conduit 20 functions as a heat conductor, conducting heat from the warming fluid passing through the inner conduit to the fluid to be warmed which flows through flow channel 22. Inner conduit 20 preferably has a wall thickness of 0.016 inches and may be in the range of from 0.014 inches to 0.025 inches. The outer diameter is preferably 0.5 inches and may be 0.498 inches to 0.502 inches.

As the warming fluid is applied to the heat exchanger, the exchanger itself will become warm. The interior tube, being of metal will necessarily expand as it is warmed and contract as it cools after use.

It is extremely important to maintain sterility when dealing with physiological fluids, and the expansion of the inner and outer conduits must be accommodated in such a manner that sterility is maintained. In accordance with the invention, outer conduit 18 is fabricated of a bio-compatible elastomeric plastic which expands or contracts along with the inner conduit. In a preferred embodiment, the outer conduit is made of polyvinylchloride and has a wall thickness of 0.060 inches. The wall thickness may be from 0.050 to 0.070 inches. The outer diameter is preferably 0.63 inches but may be from 0.62 to 0.64 inches, while the inner diameter is preferably 0.51 inches and may be from 0.502 inches to 0.520 inches.

End caps 24 and 26 overlap respective end portions of outer conduit 18 and are secured to the outer conduit by a solvent cement. The end caps are also made of bio-compatible elastomeric plastic and also accommodate some of the expansion of the inner conduit 20.

The materials from which the outer tube and end caps are fabricated also provide these elements with heat insulating capability to increase the efficiency of the heat exchanger.

The inner tube is fabricated with a helical path by a twisting operation which forms no part of this application. Other techniques for increasing the surface area of the inner conduit are known to the art. In an alternative embodiment, the outer surface of the inner tube is smooth.

Figure 3:
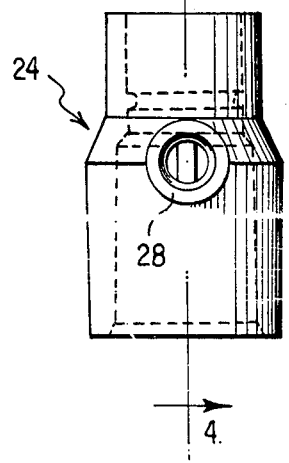
FIG. 3 is a side view of an end cap in accordance with the invention.
Figure 4:
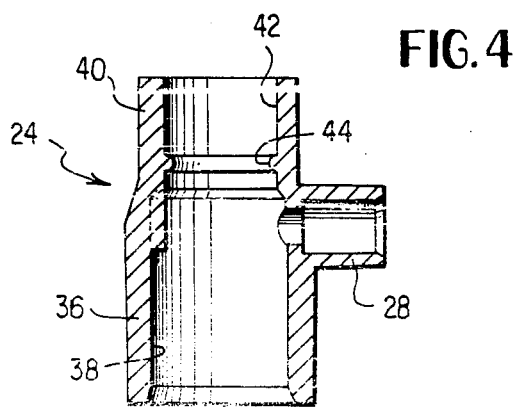
FIG. 4 is a cross section taken along line 4—4 of FIG. 3.

With reference to FIGS. 3 and 4, the details of the end caps, such as end cap 24 will be explained. A first portion 36 is hollow and provides an inner wall 38 for engaging the outer surface of outer conduit 22 and for being solvent bonded thereto. A second portion 40 is also hollow and receives a smooth-wall portion of inner conduit 20. The second portion 40 includes an inner wall 42 for tightly engaging the outer surface of inner conduit 20.

In the preferred embodiment shown in FIG. 4, the second portion further includes a protuberance in the form of an annular ring 44. This annular ring concentrates the stress on the rigid inner conduit 20 to increase the hoop strength of the second portion of the end cap. This increases the sealing strength of the assembly.

The interior diameter of wall 38 is preferably approximately 0.625 inches before assembly with outer conduit 18 to provide a tight connection. Inner wall 42 has a diameter of approximately 0.460 inches before assembly, and protuberance 44 extends radially inwardly from wall 42 by approximately 0.015 inches. Thus, before assembly the inner diameter of protuberance 44 is approximately 0.030 inches smaller than that of inner wall 42. Protuberance 44 is preferably rounded in cross-section with a radius of approximately 0.03 inches.

The above-described structure causes second portion 40 to tightly grip the outer surface of inner conduit 20 without the necessity of using a cement. As the inner tube expands with a temperature rise as discussed above, the end caps and outer conduit 18 expand also because of the elasticity of the materials used for their construction. Sterility is maintained because the section 40 tightly grips inner conduit 20 and remains stationary with respect to the inner conduit during expansion or contraction.

In the preferred embodiment, the inner and outer conduits are cylindrical and the inner walls 38 and 42 of the end caps are also cylindrical. This provides an equal distribution of pressures around the seal areas. If the heat exchanger is to be used in an environment of extreme pressures in flow channel 22, it may be desired to provide a band around the outside of second portion 40 of the end cap.

The use of the thin aluminum inner conduit and the elastomeric outer conduit produces a heat exchanger which is light, flexible and nearly unbreakable. These features facilitate manufacture and installation.

It will be appreciated that a unique heat exchanger has been described which is easily manufactured and which maintains sterility during temperature variation. Modifications within the scope of the appended claims will be apparent to those of skill in the art.

What is claimed is:

1. A heat exchanger capable of maintaining sterility during temperature variation comprising an inner conduit, an outer conduit partially covering said inner conduit and forming a fluid flow channel between an outer surface of said inner conduit and an inner surface of said outer conduit, and end cap means for securing and fluid sealing one end of said outer conduit and for communicating a first fluid with said channel, wherein said inner conduit has a thermal coefficient of expansion larger than that of said outer conduit and said outer conduit is elastic for at least partially accommodating expansion or contraction of said inner conduit, and wherein said end cap means is elastic for at least partially accommodating expansion or contraction of said inner conduit and comprises a first hollow portion cemented to said one end of said outer conduit and a second hollow portion having a hoop strength adequate to tightly grip said outer surface of said inner conduit to provide a pressure tight seal between said second hollow portion and said inner conduit and to provide a location of said pressure tight seal which remains substantially fixed with respect to said inner conduit during normal thermal expansion or contraction of said inner conduit.

2. A heat exchanger according to claim 1 wherein said outer conduit is made of an elastic plastic and said inner conduit is made of a metal.

3. A heat exchanger according to claim 2 wherein said metal is aluminum.

4. A heat exchanger according to claim 2 wherein at least a part of the exterior surface of said inner conduit is configured to provide a helical said fluid flow channel.

5. A heat exchanger according to claim 2 wherein said end cap means is made of elastic plastic.

6. A heat exchanger according to claim 5 wherein said end cap means comprises a first end cap at a first end of said outer conduit and a second end cap at an opposed end of said outer conduit.

7. A heat exchanger according to claim 1 wherein said second hollow portion comprises a protuberance extending radially inwardly and engaging said inner conduit.

8. A heat exchanger according to claim 2 wherein said inner and outer conduits are cylindrical.

9. A heat exchanger according to claim 7 wherein said inner conduit extends beyond said end cap means for providing a fluid connection to said inner conduit.

10. An end cap for sealing an end of an outer conduit to an inner conduit comprising a first hollow portion for receiving said end of an outer conduit and having an inner wall for engaging an outer wall portion of said end of an outer conduit, a second hollow portion for receiving said inner conduit, said second hollow portion having an inner wall for engaging an outer wall of said inner conduit, said second hollow portion having a protuberance extending radially inwardly for tightly engaging said outer surface of said inner conduit wherein said first and second hollow portions and said protuberance are integrally formed of elastomeric material.

11. An end cap according to claim 10 wherein said elastomeric material is polyvinylchloride.

12. A heat exchanger comprising an inner conduit, an outer conduit partially covering said inner conduit to form a flow channel between said inner and outer conduits, and two end caps, each of said end caps comprising a first hollow portion having an inner wall cemented to a portion of the outer wall of said outer conduit and a second portion comprising a second hollow portion tightly and sealingly engaging a portion of the outer wall of said inner conduit and a protuberance engaging said outer surface of said inner conduit, wherein said end caps are made of elastic material and wherein said first and second hollow portions and said protuberance are integrally formed of elastomeric material.

13. A heat exchanger capable of maintaining sterility during temperature variations comprising a metal inner conduit, an outer conduit having a length less than that of said inner conduit, an end cap at each end of said outer conduit for providing a fluid path between said inner and outer conduits, wherein each said end cap is of elastic material for at least partially accommodating expansion or contraction of said inner conduit and comprises a first hollow portion cemented to said outer conduit and a second hollow portion having a hoop strength adequate to tightly grip said inner conduit to provide a pressure tight seal at a location substantially fixed with respect to said inner conduit during expansion or contraction of said inner conduit.

* * * * *